US012607621B2

(12) United States Patent
Hayashi et al.

(10) Patent No.: US 12,607,621 B2
(45) Date of Patent: Apr. 21, 2026

(54) NON-INVASIVE SUBSTANCE ANALYZER

(71) Applicant: Mitsubishi Electric Corporation, Tokyo (JP)

(72) Inventors: Shusaku Hayashi, Tokyo (JP); Koichi Akiyama, Tokyo (JP); Yuki Tsuda, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 107 days.

(21) Appl. No.: 18/835,752

(22) PCT Filed: Feb. 17, 2022

(86) PCT No.: PCT/JP2022/006341
§ 371 (c)(1),
(2) Date: Aug. 5, 2024

(87) PCT Pub. No.: WO2023/157163
PCT Pub. Date: Aug. 24, 2023

(65) Prior Publication Data
US 2025/0137992 A1     May 1, 2025

(51) Int. Cl.
*G01N 33/49* (2006.01)
*G01N 21/17* (2006.01)
(Continued)

(52) U.S. Cl.
CPC ......... *G01N 33/49* (2013.01); *G01N 21/1717* (2013.01); *G01N 21/3577* (2013.01);
(Continued)

(58) Field of Classification Search
CPC ............... G01N 33/49; G01N 21/1717; G01N 21/3577; G01N 21/41; G01N 2021/1731;
(Continued)

(56) References Cited

U.S. PATENT DOCUMENTS 6,668,006 B1     12/2003   Margalit et al.
11,452,469 B1 *   9/2022   Aiyer ................. A61B 5/14546
(Continued)

FOREIGN PATENT DOCUMENTS

JP        2003-527625 A       9/2003
JP        2004-325128 A      11/2004
(Continued)

OTHER PUBLICATIONS

International Search Report and Written Opinion mailed on Apr. 19, 2022, received for PCT Application PCT/JP2022/006341, filed on Feb. 17, 2022, 12 pages including English Translation.
(Continued)

*Primary Examiner* — Md M Rahman
(74) *Attorney, Agent, or Firm* — XSENSUS LLP

(57)     ABSTRACT
The non-invasive substance analyzer includes an optical waveguide circuit, a probe light source, and a light intensity detector. The optical waveguide circuit has a sample mounting region. The probe light source emits probe light. The optical waveguide circuit includes a first optical waveguide to which the probe light is incident, a waveguide-type ring resonator, and a second optical waveguide. The light intensity detector detects an intensity of first light which is a part of the probe light and is optically coupled to the second optical waveguide.

16 Claims, 12 Drawing Sheets

(51) Int. Cl.
    *G01N 21/3577*     (2014.01)
    *G01N 21/41*     (2006.01)

(52) U.S. Cl.
    CPC ..... *G01N 21/41* (2013.01); *G01N 2021/1731* (2013.01); *G01N 2201/088* (2013.01)

(58) Field of Classification Search
    CPC ........... G01N 2201/088; G01N 21/171; G01N 21/7746; G01N 2021/399; G01N 2021/458; G01N 2201/0873; A61B 5/14532; A61B 5/14546; A61B 5/1455
    USPC .......................................................... 356/39
    See application file for complete search history.

(56)             References Cited

U.S. PATENT DOCUMENTS

| | | | |
|---|---|---|---|
| 11,624,615 B2 * | 4/2023 | Paniccia | G02B 6/122 |
| | | | 385/14 |
| 2013/0130254 A1 | 5/2013 | Scherer et al. | |
| 2017/0146455 A1 | 5/2017 | Mantele et al. | |
| 2021/0401291 A1 | 12/2021 | Schriek et al. | |
| 2022/0187075 A1 * | 6/2022 | Paniccia | G01C 19/66 |

FOREIGN PATENT DOCUMENTS

| | | | |
|---|---|---|---|
| JP | 2012-108095 A | 6/2012 |
| JP | 2015-502539 A | 1/2015 |
| JP | 2017-519214 A | 7/2017 |
| JP | 2022-506275 A | 1/2022 |

OTHER PUBLICATIONS

Singha et al., "On-chip Photonic Temperature Sensor Using Micro Ring Resonator", 2018 Fifteenth International Conference on Wireless and Optical Communications Networks (WOCN), Feb. 2-4, 2018, 5 pages.

Notice of Reasons for Refusal mailed on Aug. 23, 2022, received for JP Application 2022-540426, 11 pages including English Translation.

Notice of Reasons for Refusal mailed on Nov. 1, 2022, received for JP Application 2022-540426, 11 pages including English Translation.

Decision of Refusal mailed on Jan. 24, 2023, received for JP Application 2022-540426, 09 pages including English Translation.

Reconsideration Report by Examiner before Appeal mailed on May 26, 2023, received for JP Application 2022-540426, 09 pages including English Translation.

Notice of Reasons for Refusal mailed on Jan. 23, 2024, received for JP Application 2022-540426, 35 pages including English Translation.

* cited by examiner

FIG.5

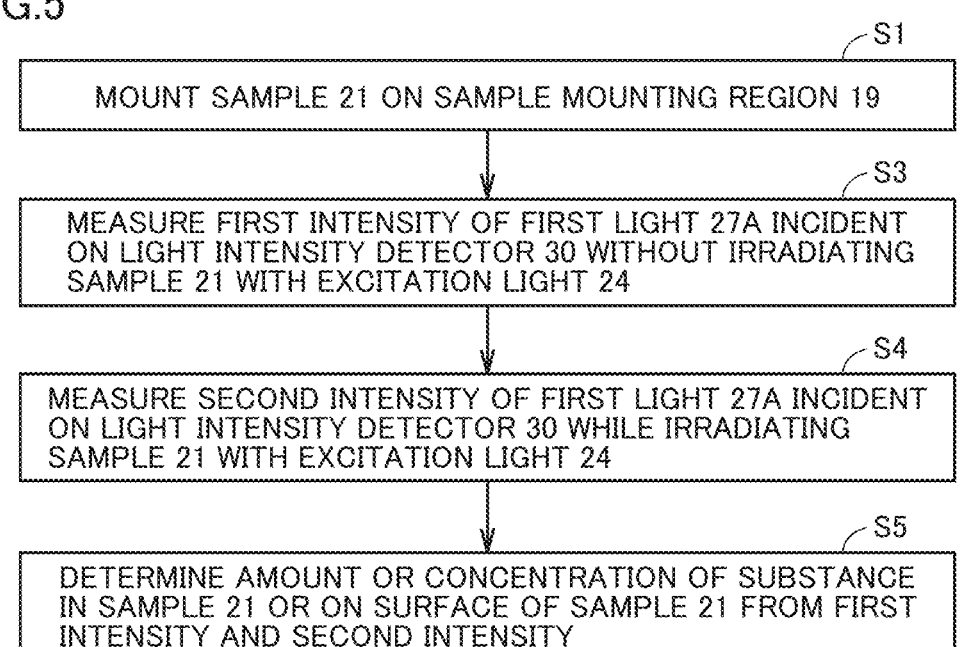

| S1 |
| MOUNT SAMPLE 21 ON SAMPLE MOUNTING REGION 19 |

| S3 |
| MEASURE FIRST INTENSITY OF FIRST LIGHT 27A INCIDENT ON LIGHT INTENSITY DETECTOR 30 WITHOUT IRRADIATING SAMPLE 21 WITH EXCITATION LIGHT 24 |

| S4 |
| MEASURE SECOND INTENSITY OF FIRST LIGHT 27A INCIDENT ON LIGHT INTENSITY DETECTOR 30 WHILE IRRADIATING SAMPLE 21 WITH EXCITATION LIGHT 24 |

| S5 |
| DETERMINE AMOUNT OR CONCENTRATION OF SUBSTANCE IN SAMPLE 21 OR ON SURFACE OF SAMPLE 21 FROM FIRST INTENSITY AND SECOND INTENSITY |

FIG.6

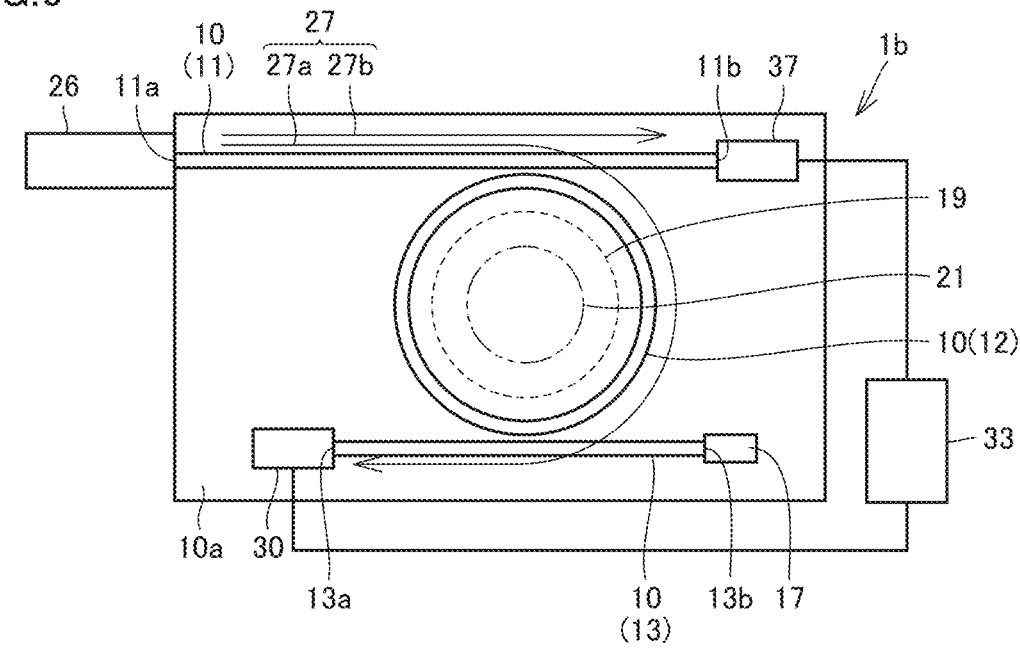

FIG.7

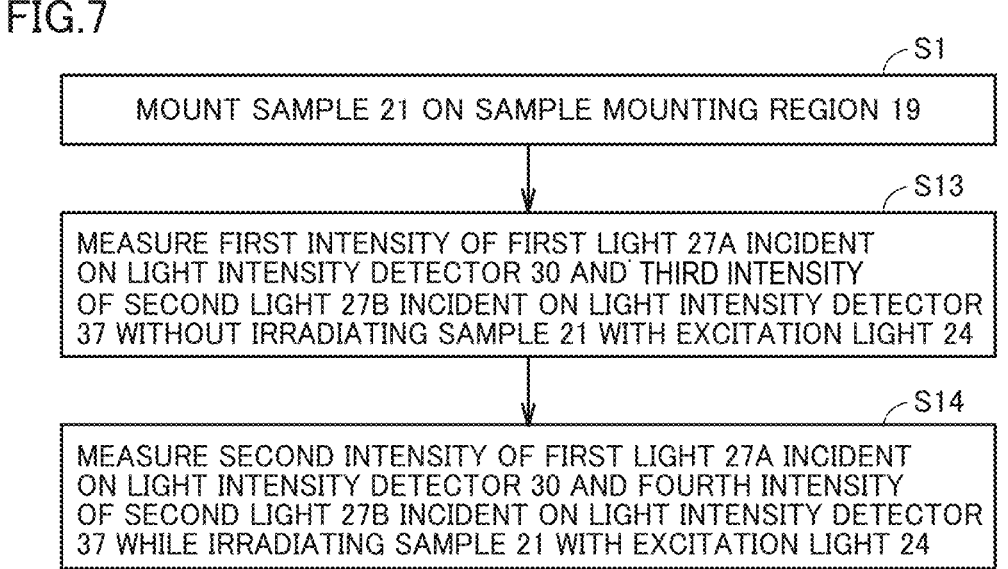

MOUNT SAMPLE 21 ON SAMPLE MOUNTING REGION 19          S1

MEASURE FIRST INTENSITY OF FIRST LIGHT 27A INCIDENT ON LIGHT INTENSITY DETECTOR 30 AND THIRD INTENSITY OF SECOND LIGHT 27B INCIDENT ON LIGHT INTENSITY DETECTOR 37 WITHOUT IRRADIATING SAMPLE 21 WITH EXCITATION LIGHT 24          S13

MEASURE SECOND INTENSITY OF FIRST LIGHT 27A INCIDENT ON LIGHT INTENSITY DETECTOR 30 AND FOURTH INTENSITY OF SECOND LIGHT 27B INCIDENT ON LIGHT INTENSITY DETECTOR 37 WHILE IRRADIATING SAMPLE 21 WITH EXCITATION LIGHT 24          S14

DETERMINE AMOUNT OR CONCENTRATION OF SUBSTANCE IN SAMPLE 21 OR ON SURFACE OF SAMPLE 21 FROM FIRST INTENSITY, SECOND INTENSITY, THIRD INTENSITY AND FOURTH INTENSITY          S15

FIG.8

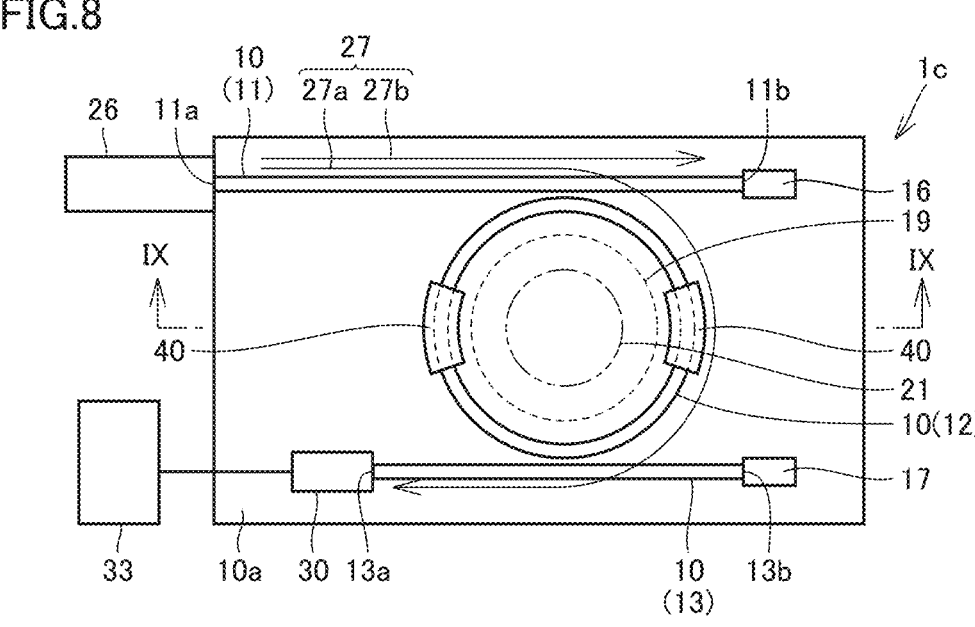

FIG.11

S1
MOUNT SAMPLE 21 ON SAMPLE MOUNTING REGION 19

S2
REGULATE INITIAL PHASE OF WAVEGUIDE-TYPE RING RESONATOR 12 BY USING THERMOREGULATOR 40

S3
MEASURE FIRST INTENSITY OF FIRST LIGHT 27A INCIDENT ON LIGHT INTENSITY DETECTOR 30 WITHOUT IRRADIATING SAMPLE 21 WITH EXCITATION LIGHT 24

S4
MEASURE SECOND INTENSITY OF FIRST LIGHT 27A INCIDENT ON LIGHT INTENSITY DETECTOR 30 WHILE IRRADIATING SAMPLE 21 WITH EXCITATION LIGHT 24

S5
DETERMINE AMOUNT OR CONCENTRATION OF SUBSTANCE IN SAMPLE 21 OR ON SURFACE OF SAMPLE 21 FROM FIRST INTENSITY AND SECOND INTENSITY

FIG.12

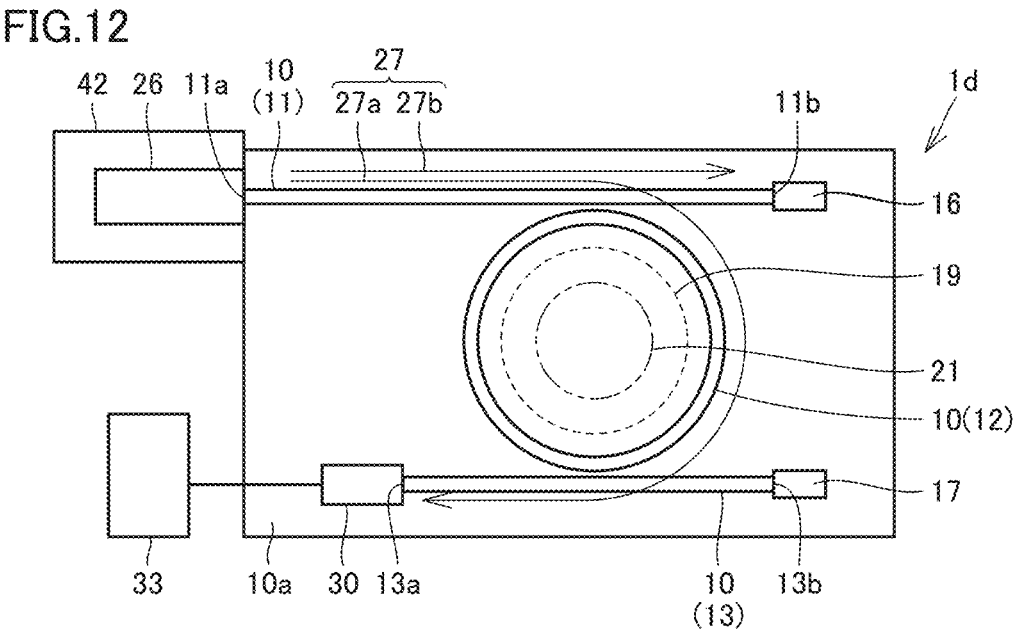

NON-INVASIVE SUBSTANCE ANALYZER

CROSS-REFERENCE TO RELATED APPLICATION

This application is a national stage application, pursuant to 35 U.S.C. § 371, of International Patent Application No. PCT/JP2022/006341, filed Feb. 17, 2022, the entire contents of which are incorporated herein by reference.

TECHNICAL FIELD

The present disclosure relates to a non-invasive substance analyzer.

BACKGROUND ART

Japanese Patent Laying-Open No. 2017-519214 (PTL 1) discloses a non-invasive analysis system that includes an optical medium, an infrared light source, a probe light source, and a photodiode. Specifically, a biological sample is mounted on the optical medium. The infrared light source emits infrared light. The infrared light passes through the optical medium, and is irradiated on the biological sample. The infrared light is absorbed by the biological sample, and thereby the biological sample generates heat. The amount of absorption heat in a biological sample depends on the amount or concentration of biological components in the sample or on the surface of the sample.

The probe light source emits probe light, which is visible light, toward the optical medium. The probe light is totally internally reflected at an interface between the optical medium and the biological sample and exits from the optical medium. The heat absorbed by the biological sample is transferred to the optical medium, which changes the refractive index of the optical medium. The change in the refractive index of the optical medium affects the total internal reflection of the probe light at the interface between the optical medium and the biological sample, which changes the travelling direction of the probe light exiting from the optical medium. The photodiode functions as an optical position sensor to detect a change in the travelling direction of the probe light. The amount or concentration of a biological component is measured from the change in the travelling direction of the probe light detected by the photodiode. For example, if the sample is a patient's skin, the patient's blood glucose level is measured as a biological component.

CITATION LIST

Patent Literature

PTL 1: Japanese Patent Laying-Open No. 2017-519214

SUMMARY OF INVENTION

Technical Problem

However, in the non-invasive analysis system disclosed in PTL 1, the photodiode has a large size so as to cope with the change in the travelling direction of the probe light. Therefore, it is difficult to miniaturize the non-invasive analysis system. The present disclosure has been made in view of the above-mentioned problem, and an object of the present disclosure is to provide a non-invasive substance analyzer that can be miniaturized.

Solution to Problem

The non-invasive substance analyzer of the present disclosure includes an optical waveguide circuit, an excitation light source, a probe light source, and a first light intensity detector. The optical waveguide circuit has a first main surface including a sample mounting region and a second main surface opposite to the first main surface. The excitation light source emits excitation light toward a sample mounted on the sample mounting region. The probe light source emits probe light. The optical waveguide circuit includes a first optical waveguide to which the probe light is incident, a waveguide-type ring resonator which is optically coupled to the first optical waveguide, and a second optical waveguide which is optically coupled to the waveguide-type ring resonator. The first light intensity detector is optically coupled to the second optical waveguide and detects an intensity of first light which is a part of the probe light and is optically coupled to the second optical waveguide.

Advantageous Effects of Invention

In the non-invasive substance analyzer of the present disclosure, the first light intensity detector detects a change in the intensity of the probe light coupled to the second optical waveguide due to the ON/OFF of the excitation light instead of a change in the position of the probe light due to the ON/OFF of the excitation light. Therefore, the first light intensity detector is miniaturized, and thereby the non-invasive substance analyzer is miniaturized.

BRIEF DESCRIPTION OF DRAWINGS

FIG. 5 is a flowchart of a non-invasive substance analysis method according to the first embodiment;

FIG. 6 is a schematic plan view of a non-invasive substance analyzer according to a second embodiment;

FIG. 7 is a flowchart of a non-invasive substance analysis method according to the second embodiment;

FIG. 8 is a schematic plan view of a non-invasive substance analyzer according to a third embodiment;

FIG. 11 is a flowchart of a non-invasive substance analysis method according to the third embodiment;

FIG. 12 is a schematic plan view of a non-invasive substance analyzer according to a fourth embodiment;

DESCRIPTION OF EMBODIMENTS

Figure 1:
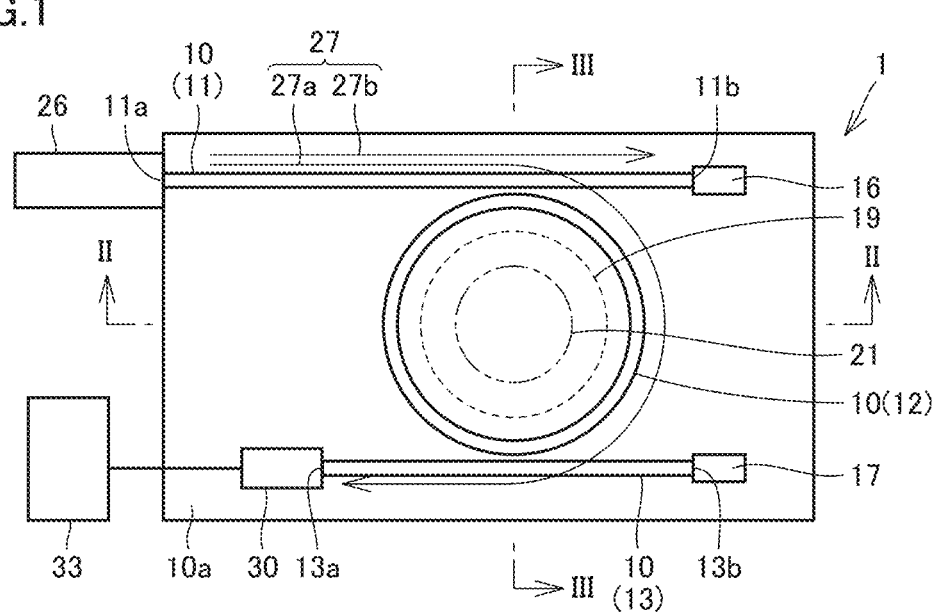
FIG. 1 is a schematic plan view of a non-invasive substance analyzer according to a first embodiment.

Hereinafter, embodiments will be described. The same components will be denoted by the same reference numerals, and the description thereof will not be repeated.

First Embodiment

Figure 2:
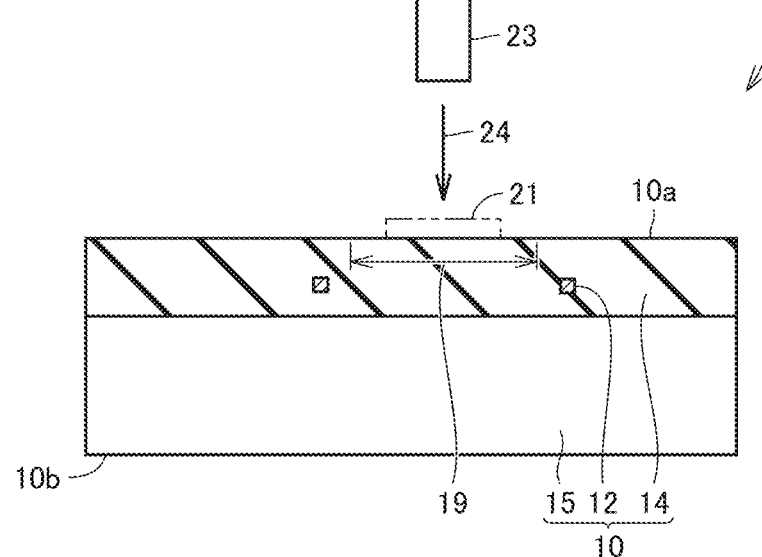
FIG. 2 is a schematic cross-sectional view of the non-invasive substance analyzer according to the first embodiment taken along a cross-sectional line II-II illustrated in FIG. 1.
Figure 3:
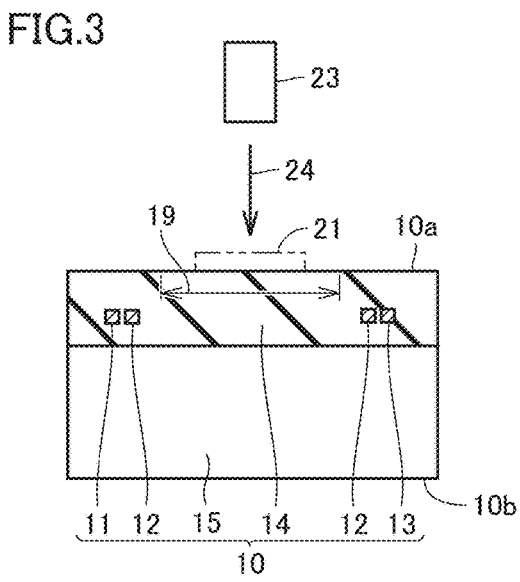
FIG. 3 is a schematic cross-sectional view of the non-invasive substance analyzer according to the first embodiment taken along a cross-sectional line III-III illustrated in FIG. 1.

A non-invasive substance analyzer 1 according to a first embodiment will be described with reference to FIGS. 1 to 4. With reference to FIGS. 1 to 3, the non-invasive substance analyzer 1 mainly includes an optical waveguide circuit 10, an excitation light source 23, a probe light source 26, a light intensity detector 30, and a substance analysis unit 33.

With reference to FIG. 1, the probe light source 26 emits probe light 27. The probe light source 26 is, for example, a laser light source such as a laser diode. In the present embodiment, the probe light source 26 is disposed outside the optical waveguide circuit 10. The probe light source 26 may be disposed on a substrate 15.

The wavelength of the probe light 27 is, for example, 1100 nm or more. The wavelength of the probe light 27 may be 1300 nm or more. The wavelength of the probe light 27 is, for example, 1700 nm or less. Thus, an inexpensive laser diode for optical communication such as an InGaAsP laser diode or an InGaNAs laser diode may be used as the probe light source 26. Further, since the probe light 27 is not visible light, the risk for the probe light 27 to damage the human eye may be reduced. The output of the probe light 27 is, for example, 5 mW or less. Therefore, the risk for probe light 27 to damage the human eye may be reduced.

With reference to FIGS. 1 to 3, the optical waveguide circuit 10 has a main surface 10a and a main surface 10b opposite to the main surface 10a. The optical waveguide circuit 10 includes a substrate 15, a first optical waveguide 11, a waveguide-type ring resonator 12, a second optical waveguide 13, and a cladding layer 14. The optical waveguide circuit 10 may further include termination portions 16 and 17.

The substrate 15 supports the first optical waveguide 11, the waveguide-type ring resonator 12, the second optical waveguide 13, and the cladding layer 14. The substrate 15 has a main surface 10b. The substrate 15 is, for example, a silicon substrate.

The probe light 27 is incident on the first optical waveguide 11 of the optical waveguide circuit 10. The first optical waveguide 11 includes an end 11a to which the probe light 27 is incident and an end 11b opposite to the end 11a. The first optical waveguide 11 has a higher refractive index than the cladding layer 14. The probe light 27 propagates in the first optical waveguide 11. The first optical waveguide 11 is, for example, a silicon waveguide.

The waveguide-type ring resonator 12 is optically coupled to the first optical waveguide 11. The waveguide-type ring resonator 12 has a higher refractive index than the cladding layer 14. The probe light 27 propagates in the waveguide-type ring resonator 12. The waveguide-type ring resonator 12 has a thermo-optical effect. The waveguide-type ring resonator 12 is, for example, a silicon waveguide. The thermo-optical coefficient of silicon is $2.3 \times 10^{-4}$ ($K^{-1}$). Silicon has a relatively large thermo-optical coefficient among optical materials for optical waveguides.

The second optical waveguide 13 is optically coupled to the waveguide-type ring resonator 12. The second optical waveguide 13 has a higher refractive index than the cladding layer 14. The probe light 27 propagates in the second optical waveguide 13. In a plan view of the main surface 10a, the second optical waveguide 13 is disposed symmetrically to the first optical waveguide 11 with respect to the waveguide-type ring resonator 12. The second optical waveguide 13 includes an end 13a optically coupled to the light intensity detector 30 and an end 13b opposite to the end 13a. The ends 11a and 13a are on the same side of the waveguide-type ring resonator 12. The ends 11b and 13b are on the same side of the waveguide-type ring resonator 12.

The cladding layer 14 separates the first optical waveguide 11, the waveguide-type ring resonator 12, and the second optical waveguide 13 from the substrate 15. The cladding layer 14 covers the first optical waveguide 11, the waveguide-type ring resonator 12, and the second optical waveguide 13. The cladding layer 14 has a main surface 10a. The thermal conductivity of the cladding layer 14 is smaller than the thermal conductivity of the substrate 15. The cladding layer 14 is made of, for example, silica glass.

Figure 4:
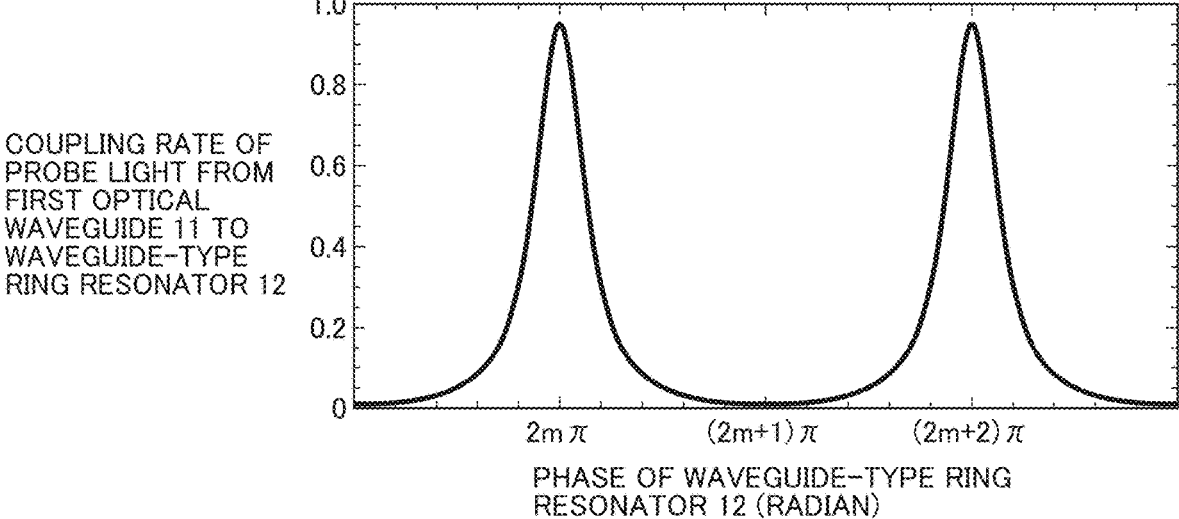
FIG. 4 is a graph illustrating a relationship between a phase of a waveguide-type ring resonator and a coupling rate of probe light from a first optical waveguide to the waveguide-type ring resonator.

The probe light 27 incident on the first optical waveguide 11 from the probe light source 26 is mainly divided into first light 27a which is optically coupled to the second optical waveguide 13 via the waveguide-type ring resonator 12 and second light 27b which propagates in the first optical waveguide 11 without being coupled to the waveguide-type ring resonator 12. FIG. 4 illustrates a coupling rate of the probe light 27 from the first optical waveguide 11 to the waveguide-type ring resonator 12. The coupling rate of the probe light 27 from the waveguide-type ring resonator 12 to the second optical waveguide 13 is the same as the coupling rate of the probe light 27 from the first optical waveguide 11 to the waveguide-type ring resonator 12. The horizontal axis in FIG. 4 represents a phase of the waveguide-type ring resonator 12 with respect to the wavelength of the probe light 27, which is defined by the following equation (1).

$$\text{Phase of the waveguide-type ring resonator } 12 = 2\pi \times (nL)/\lambda \qquad (1)$$

5

6

Where n represents a refractive index of the waveguide-type ring resonator 12, L represents a length of the waveguide-type ring resonator 12, NL represents an optical path length of the waveguide-type ring resonator 12, and λ represents the wavelength of the probe light 27. In FIG. 4, m is a natural number.

When the phase of the waveguide-type ring resonator 12 is an even multiple of π, the coupling rate of the probe light 27 from the first optical waveguide 11 to the waveguide-type ring resonator 12 is maximum. As the phase of the waveguide-type ring resonator 12 gets closer to an even number multiple of π from an odd number multiple of π, the coupling rate of the probe light 27 from the first optical waveguide 11 to the waveguide-type ring resonator 12 changes more rapidly.

The free spectral region Δf of the waveguide-type ring resonator 12 (i.e., the interval of a frequency at which the coupling rate of the probe light 27 from the first optical waveguide 11 to the waveguide-type ring resonator 12 is maximum) is given by equation (2), $$\Delta f = c/(nL) = (f\lambda)/(nL) \qquad (2)$$

Where c represents light speed in vacuum.

With reference to the equations (1) and (2), when the refractive index n of the waveguide-type ring resonator 12 or the wavelength λ of the probe light 27 changes, the phase and the free spectrum region Δf of the waveguide-type ring resonator 12 change, which causes the coupling rate of the probe light 27 from the first optical waveguide 11 to the waveguide-type ring resonator 12 to change.

With reference to FIG. 1, the termination portion 16 is provided at the end 11b of the first optical waveguide 11. The termination portion 17 is provided at the end 13b of the second optical waveguide 13. The termination portion 16 or 17 is a light scatterer that scatters the probe light 27 or a light absorber that absorbs the probe light 27. The termination portion 16 or 17 scatters or absorbs the probe light 27 to reduce the return light of the probe light 27 that travels to the waveguide-type ring resonator 12, the probe light source 26, and the light intensity detector 30. The termination portion 16 or 17 is formed from, for example, a tapered waveguide that easily scatters light to the outside of the waveguide and an electrode (for example, a metal electrode) that absorbs scattered light.

With reference to FIGS. 1 to 3, the main surface 10a of the optical waveguide circuit 10 includes a sample mounting region 19 on which a sample 21 is mounted. The sample 21 is, for example, a patient's skin or body fluid. In a plan view of the main surface 10a, the sample mounting region 19 is located inside the waveguide-type ring resonator 12, and is surrounded by the waveguide-type ring resonator 12.

With reference to FIGS. 2 and 3, the excitation light source 23 emits excitation light 24 toward the sample 21 mounted on the sample mounting region 19. The wavelength of the excitation light 24 is determined according to the absorption wavelength of a substance in the sample 21 or on the surface of the sample 21. The wavelength of the excitation light 24 may be longer than the wavelength of the probe light 27. The excitation light 24 is, for example, mid-infrared light. The wavelength of the excitation light 24 is, for example, 6.0 µm or more. The wavelength of the excitation light 24 may be 8.0 µm or more. The wavelength of the excitation light 24 is, for example, 13.0 µm or less. The wavelength of the excitation light 24 may be 11.0 µm or less. The excitation light 24 may have a plurality of wavelengths. For example, when the noninvasive substance analyzer 1 is used to measure the blood glucose level of a patient, the wavelength range of the excitation light 24 is such a wavelength range that includes the wavelength of the fingerprint spectrum of blood sugar (for example, a wavelength range of 8.5 µm or more and 10 µm or less). The excitation light source 23 is, for example, a quantum cascade laser that can emit broadband mid-infrared light. The sample 21 may be irradiated with the excitation light 24 together with reference light that is not absorbed by the substance in the sample 21 or on the surface of the sample 21.

The excitation light 24 is absorbed by the substance in the sample 21 or on the surface of the sample 21. The absorption of the excitation light 24 by the substance generates absorption heat in the sample 21. The absorption heat in the sample 21 is conducted to the waveguide-type ring resonator 12, which causes the temperature of the waveguide-type ring resonator 12 to change. The waveguide-type ring resonator 12 has a thermo-optical effect. Therefore, when the temperature of the waveguide-type ring resonator 12 changes, the refractive index of the waveguide-type ring resonator 12 changes, which causes the coupling rate of the probe light 27 from the first optical waveguide 11 to the second optical waveguide 13 via the waveguide-type ring resonator 12 to change.

The substance in the sample 21 or on the surface of the sample 21 is, for example, a biological component. Specifically, when the non-invasive substance analyzer 1 is used to measure the blood glucose level of a patient, the substance to be analyzed by the non-invasive substance analyzer 1 is blood sugar contained in interstitial fluid in the epidermal tissue of the patient.

In the present embodiment, the excitation light source 23 is disposed to face the main surface 10a. The excitation light 24 is incident on the sample 21 from the side of the main surface 10a. The excitation light 24 is incident on the sample 21 without passing through the substrate 15. If the substrate 15 is transparent to the excitation light 24, the excitation light source 23 may be disposed opposite to the main surface 10b of the optical waveguide circuit 10, and the excitation light 24 may be incident on the sample 21 through the substrate 15.

With reference to FIG. 1, the light intensity detector 30 is optically coupled to the end 13a of the second optical waveguide 13. The light intensity detector 30 detects the intensity of the first light 27a which is a part of the probe light 27 and is optically coupled to the second optical waveguide 13. The light intensity detector 30 measures a first intensity of the first light 27a incident on the light intensity detector 30 when the sample 21 is not irradiated with the excitation light 24 and a second intensity of the first light 27a incident on the light intensity detector 30 when the sample 21 is irradiated with the excitation light 24. As described above, between a time when the sample 21 is not irradiated with the excitation light 24 and a time when the sample 21 is irradiated with the excitation light 24, the temperature of the waveguide-type ring resonator 12 changes, which causes the coupling rate of the probe light 27 from the first optical waveguide 11 to the second optical waveguide 13 via the waveguide-type ring resonator 12 to change. Therefore, the second intensity of the first light 27a is different from the first intensity of the first light 27a.

The light intensity detector 30 outputs the first intensity of the first light 27a and the second intensity of the first light 27a to the substance analysis unit 33. The light intensity detector 30 is, for example, a photodiode such as a SiGe photodiode. In the present embodiment, the light intensity detector 30 is disposed on the substrate 15. The light intensity detector 30 may be disposed outside the optical waveguide circuit 10.

The non-invasive substance analyzer 1 analyzes the substance based on the intensity of the first light 27a which is a part of the probe light 27 and is optically coupled to the second optical waveguide 13. With reference to FIG. 1, the substance analysis unit 33 is connected to the light intensity detector 30. The substance analysis unit 33 receives the first intensity of the first light 27a and the second intensity of the first light 27a from the light intensity detector 30. The substance analysis unit 33 determines the type, amount, or concentration of the substance in the sample 21 or on the surface of the sample 21 from the first intensity of the first light 27a and the second intensity of the first light 27a.

The substance analysis unit 33 is, for example, a microcomputer that includes a processor, a random access memory (RAM), and a storage device such as a read only memory (ROM). As the processor, for example, a CPU (Central Processing Unit) may be employed. The RAM functions as a working memory that temporarily stores data to be processed by the processor. The storage device stores, for example, a program to be executed by the processor. In the present embodiment, when the processor executes the program stored in the storage device, the substance analysis unit 33 determines the type of the substance in the sample 21 or on the surface of the sample 21 or calculates the amount or concentration of the substance in the sample 21 or on the surface of the sample 21 from the first intensity of the first light 27a and the second intensity of the first light 27a. The various processes in the substance analysis unit 33 are not limited to being executed by software, and may be executed by dedicated hardware (electronic circuit).

A non-invasive substance analysis method of the present embodiment using the non-invasive substance analyzer 1 will be described with reference mainly to FIG. 5.

The non-invasive substance analysis method of the present embodiment includes mounting the sample 21 on the sample mounting region 19 (S1). When there is a difference between the temperature of the optical waveguide circuit 10 and the temperature of the sample 21, heat transfer occurs between the optical waveguide circuit 10 and the sample 21. This heat transfer makes it difficult to detect a change in the coupling rate of the probe light 27 from the first optical waveguide 11 to the second optical waveguide 13 via the waveguide-type ring resonator 12 due to the absorption heat in the sample 21, which makes it difficult to analyze the substance in the sample 21 or on the surface of the sample 21. Therefore, step S3 to be described later is not performed until a thermal equilibrium is achieved between the optical waveguide circuit 10 and the sample 21. After the thermal equilibrium is achieved between the optical waveguide circuit 10 and the sample 21, the non-invasive substance analyzer 1 is used to analyze the substance in the sample 21 or on the surface of the sample 21.

The non-invasive substance analysis method of the present embodiment includes measuring the first intensity of the first light 27a incident on the light intensity detector 30 without irradiating the sample 21 with the excitation light 24 (S3). Since the sample 21 is not irradiated with the excitation light 24 (an OFF state of the excitation light 24), absorption heat is not generated in the sample 21.

The non-invasive substance analysis method of the present embodiment includes measuring the second intensity of the first light 27a incident on the light intensity detector 30 while irradiating the sample 21 with the excitation light 24

(S4). Since the sample 21 is irradiated with the excitation light 24 (an ON state of the excitation light 24), the excitation light 24 is absorbed by the substance in the sample 21 or on the surface of the sample 21. Absorption heat is generated in the sample 21. The absorption heat in the sample 21 is conducted to the waveguide-type ring resonator 12. The temperature of the waveguide-type ring resonator 12 changes, and thereby the refractive index of the waveguide-type ring resonator 12 changes. Accordingly, the coupling rate of the probe light 27 from the first optical waveguide 11 to the second optical waveguide 13 via the waveguide-type ring resonator 12 changes. Therefore, the second intensity of the first light 27a is different from the first intensity of the first light 27a.

The non-invasive substance analysis method of the present embodiment includes determining the amount or concentration of the substance in the sample 21 or on the surface of the sample 21 from the first intensity of the first light 27a and the second intensity of the first light 27a (S5). For example, the substance analysis unit 33 is connected to a memory (not shown). The memory stores a data table in which the wavelength of the excitation light 24 is associated with the type of the substance, and a data table in which the difference between the first intensity and the second intensity is associated with the amount or concentration of the substance. The substance analysis unit 33 determines the type of the substance, and calculates the amount or concentration of the substance with reference to these data tables.

Effects of the non-invasive substance analyzer 1 of the present embodiment will be described.

The non-invasive substance analyzer 1 of the present embodiment includes an optical waveguide circuit 10, an excitation light source 23, a probe light source 26, and a first light intensity detector (a light intensity detector 30). The optical waveguide circuit 10 has a first main surface (a main surface 10a) including a sample mounting region 19 and a second main surface (a main surface 10b) opposite to the first main surface. The excitation light source 23 emits excitation light 24 toward a sample 21 mounted on the sample mounting region 19. The probe light source 26 emits probe light 27. The optical waveguide circuit 10 includes a first optical waveguide 11 to which the probe light 27 is incident, a waveguide-type ring resonator 12 which is optically coupled to the first optical waveguide 11, and a second optical waveguide 13 which is optically coupled to the waveguide-type ring resonator 12. The first light intensity detector is optically coupled to the second optical waveguide 13, and detects the intensity of the first light 27a which is a part of the probe light 27 and is optically coupled to the second optical waveguide 13.

The first light intensity detector (the light intensity detector 30) detects a change in the intensity of the first light 27a coupled to the second optical waveguide 13 due to the ON/OFF of the excitation light 24 instead of a change in the position of the probe light 27 due to the ON/OFF of the excitation light 24. Therefore, the first light intensity detector is miniaturized, and thereby the non-invasive substance analyzer 1 is miniaturized.

In the non-invasive substance analyzer 1 of the present embodiment, the sample mounting region 19 is located inside the waveguide-type ring resonator 12 in a plan view of the first main surface (the main surface 10a).

In a plan view of the first main surface (the main surface 10a), the sample mounting region 19 is surrounded by the waveguide-type ring resonator 12. The absorption heat in the sample 21 is efficiently conducted to the waveguide-type ring resonator 12. The change in the intensity of the first light 27a due to the ON/OFF of the excitation light 24 becomes greater. Therefore, the non-invasive substance analyzer 1 can analyze the substance in the sample 21 or on the surface of the sample 21 with higher accuracy.

The non-invasive substance analyzer 1 according to the present embodiment further includes a substance analysis unit 33 that analyzes a substance in the sample 21 or on the surface of the sample 21 based on the intensity of the first light 27a. Therefore, the non-invasive substance analyzer 1 is miniaturized.

In the non-invasive substance analyzer 1 of the present embodiment, the optical waveguide circuit 10 includes a first termination portion (a termination portion 17). The second optical waveguide 13 includes a first end (an end 13a) optically coupled to the first light intensity detector (the light intensity detector 30) and a second end (an end 13b) opposite to the first end. The first termination portion is provided at the second end of the second optical waveguide 13, and scatters or absorbs the probe light 27.

The first termination portion (the termination portion 17) scatters or absorbs the probe light 27 to prevent the return light of the probe light 27 from being coupled to the waveguide-type ring resonator 12, the probe light source 26, and the first light intensity detector (the light intensity detector 30). Therefore, the non-invasive substance analyzer 1 can analyze the substance in the sample 21 or on the surface of the sample 21 with higher accuracy.

In the non-invasive substance analyzer 1 of the present embodiment, the optical waveguide circuit 10 includes a second termination portion (a termination portion 16). The first optical waveguide 11 includes a third end (an end 11a) to which the probe light 27 is incident and a fourth end (an end 11b) opposite to the third end. The second termination portion is provided at the fourth end of the first optical waveguide 11, and scatters or absorbs the probe light 27.

The second termination portion (the termination portion 16) scatters or absorbs the probe light 27 to prevent the return light of the probe light 27 from being coupled to the waveguide-type ring resonator 12, the probe light source 26, and the first light intensity detector (the light intensity detector 30). Therefore, the non-invasive substance analyzer 1 can analyze the substance in the sample 21 or on the surface of the sample 21 with higher accuracy.

In the non-invasive substance analyzer 1 of the present embodiment, the waveguide-type ring resonator 12 is a silicon waveguide.

Silicon has a relatively large thermo-optical coefficient among optical materials for optical waveguides. Therefore, even if the amount of absorption heat in the sample 21 is small due to reasons such as the amount of the substance in the sample 21 or on the surface of the sample 21 is small, the change in the intensity of the first light 27a due to the ON/OFF of the excitation light 24 becomes large. Thereby, the non-invasive substance analyzer 1 can analyze the substance in the sample 21 or on the surface of the sample 21 with higher accuracy.

Second Embodiment

A non-invasive substance analyzer 1b according to a second embodiment will be described with reference to FIG. 6. The non-invasive substance analyzer 1b of the present embodiment has a configuration similar to that of the non-invasive substance analyzer 1 of the first embodiment, but is mainly different in the following points.

The non-invasive substance analyzer 1b includes a light intensity detector 37 in place of the termination portion 16

(see FIG. 1). The light intensity detector 37 is optically coupled to the end 11b of the first optical waveguide 11. The light intensity detector 37 detects the intensity of the second light 27b which is a part of the probe light 27 and propagates in the first optical waveguide 11 without being coupled to the waveguide-type ring resonator 12.

The non-invasive substance analyzer 1b analyzes the substance in the sample 21 or on the surface of the sample 21 based on the intensity of the first light 27a which is a part of the probe light 27 and is optically coupled to the second optical waveguide 13 and the intensity of the second light 27b which is a part of the probe light 27 and propagates in the first optical waveguide 11 without being coupled to the waveguide-type ring resonator 12. For example, the non-invasive substance analyzer 1b analyzes the substance in the sample 21 or on the surface of the sample 21 based on a difference between the intensity of the first light 27a which is a part of the probe light 27 and is optically coupled to the second optical waveguide 13 and the intensity of the second light 27b which is a part of the probe light 27 and propagates in the first optical waveguide 11 without being coupled to the waveguide-type ring resonator 12.

Specifically, the light intensity detector 37 measures a third intensity of the second light 27b incident on the light intensity detector 37 when the sample 21 is not irradiated with the excitation light 24 and a fourth intensity of the second light 27b incident on the light intensity detector 37 when the sample 21 is irradiated with the excitation light 24. As described in the first embodiment, between a time when the sample 21 is not irradiated with the excitation light 24 and a time when the sample 21 is irradiated with the excitation light 24, the temperature of the waveguide-type ring resonator 12 changes, which causes the coupling rate of the probe light 27 from the first optical waveguide 11 to the second optical waveguide 13 via the waveguide-type ring resonator 12 to change. Therefore, the fourth intensity of the second light 27b is different from the third intensity of the second light 27b.

The light intensity detector 37 outputs the third intensity of the second light 27b and the fourth intensity of the second light 27b to the substance analysis unit 33. The light intensity detector 37 is, for example, a photodiode such as a SiGe photodiode. In the present embodiment, the light intensity detector 37 is disposed on the substrate 15. The light intensity detector 37 may be disposed outside the optical waveguide circuit 10.

The substance analysis unit 33 is also connected to a light intensity detector 37 in addition to the light intensity detector 30. The substance analysis unit 33 receives the first intensity of the first light 27a and the second intensity of the first light 27a from the light intensity detector 30, and receives the third intensity of the second light 27b and the fourth intensity of the second light 27b from the light intensity detector 37, The substance analysis unit 33 determines the type, amount, or concentration of the substance in the sample 21 or on the surface of the sample 21 from the first intensity of the first light 27a, the second intensity of the first light 27a, the third intensity of the second light 27b, and the fourth intensity of the second light 27b.

A non-invasive substance analysis method of the present embodiment using the non-invasive substance analyzer 1b will be described with reference mainly to FIG. 7. The non-invasive substance analysis method of the present embodiment is similar to the non-invasive substance analysis method of the first embodiment, but is different from the non-invasive substance analysis method of the first embodiment in the following points.

The non-invasive substance analysis method of the present embodiment includes, subsequent to step S1, measuring the first intensity of the first light 27a incident on the light intensity detector 30 and the third intensity of the second light 27b incident on the light intensity detector 37 without irradiating the sample 21 with the excitation light 24 (S13). Since the sample 21 is not irradiated with the excitation light 24 (an OFF state of the excitation light 24), absorption heat is not generated in the sample 21.

The non-invasive substance analysis method of the present embodiment includes measuring the second intensity of the first light 27a incident on the light intensity detector 30 and the fourth intensity of the second light 27b incident on the light intensity detector 37 while irradiating the sample 21 with the excitation light 24 (S14). Since the sample 21 is irradiated with the excitation light 24 (an ON state of the excitation light 24), the excitation light 24 is absorbed by the substance in the sample 21 or on the surface of the sample 21. Absorption heat is generated in the sample 21. The absorption heat in the sample 21 is conducted to the waveguide-type ring resonator 12. The temperature of the waveguide-type ring resonator 12 changes, and thereby the refractive index of the waveguide-type ring resonator 12 changes. Accordingly, the coupling rate of the probe light 27 from the first optical waveguide 11 to the second optical waveguide 13 via the waveguide-type ring resonator 12 changes. Therefore, the second intensity of the first light 27a is different from the first intensity of the first light 27a. The fourth intensity of the second light 27b is different from the third intensity of the second light 27b.

The non-invasive substance analysis method of the present embodiment includes determining the amount or concentration of the substance in the sample 21 or on the surface of the sample 21 from the first intensity of the first light 27a, the second intensity of the first light 27a, the third intensity of the second light 27b, and the fourth intensity of the second light 27b (S15). For example, the substance analysis unit 33 calculates a difference between the first intensity of the first light 27a and the third intensity of the second light 27b as a first difference signal when the excitation light 24 is turned off. The substance analysis unit 33 calculates a difference between the second intensity of the first light 27a and the fourth intensity of the second light 27b as a second difference signal when the excitation light 24 is turned on. The memory stores a data table in which the wavelength of the excitation light 24 is associated with the type of the substance, and a data table in which a difference between the first difference signal and the second difference signal is associated with the amount or concentration of the substance. The substance analysis unit 33 determines the type of the substance and calculates the amount or concentration of the substance with reference to these data tables.

The non-invasive substance analyzer 1b of the present embodiment further exhibits the following effects in addition to the effects of the non-invasive substance analyzer 1 of the first embodiment.

The non-invasive substance analyzer 1b of the present embodiment further includes a second light intensity detector (a light intensity detector 37). The second light intensity detector is optically coupled to the first optical waveguide 11, and detects the intensity of the second light 27b which is a part of the probe light 27 and propagates in the first optical waveguide 11 without being coupled to the waveguide-type ring resonator 12.

The non-invasive substance analyzer 1b can analyze the substance in the sample 21 or on the surface of the sample 21 based on the difference between the intensity of the first light 27a measured by the first light intensity detector (the light intensity detector 30) and the intensity of the second light 27b measured by the second light intensity detector (the light intensity detector 37). The intensity of the first light 27a may include a noise component due to a small disturbance in the optical waveguide circuit 10. The small disturbance is, for example, roughness of a light incident surface of the optical waveguide circuit 10 and roughness of a side wall of the optical waveguide due to a manufacturing process. By determining the difference between the intensity of the first light 27a and the intensity of the second light 27b, the noise component in the intensity of the first light 27a is canceled by the noise component in the intensity of the second light 27b. Therefore, the difference between the intensity of the first light 27a and the intensity of the second light 27b has a higher S/N ratio than the intensity of the first light 27a. The non-invasive substance analyzer 1b can analyze the substance in the sample 21 or on the surface of the sample 21 with higher accuracy.

The non-invasive substance analyzer 1b of the present embodiment further includes a substance analysis unit 33 that analyzes a substance in the sample 21 or on the surface of the sample 21 based on a difference between the intensity of the first light 27a and the intensity of the second light 27b.

By determining the difference between the intensity of the first light 27a and the intensity of the second light 27b, the noise component in the intensity of the first light 27a is canceled by the noise component in the intensity of the second light 27b. Therefore, the difference between the intensity of the first light 27a and the intensity of the second light 27b has a higher S/N ratio than the intensity of the first light 27a. The non-invasive substance analyzer 1b can analyze the substance in the sample 21 or on the surface of the sample 21 with higher accuracy.

Third Embodiment

A non-invasive substance analyzer 1c according to a third embodiment will be described with reference to FIGS. 8 to 10. The non-invasive substance analyzer 1c of the present embodiment has a configuration similar to that of the non-invasive substance analyzer 1 of the first embodiment, but is mainly different in the following points.

Figure 9:
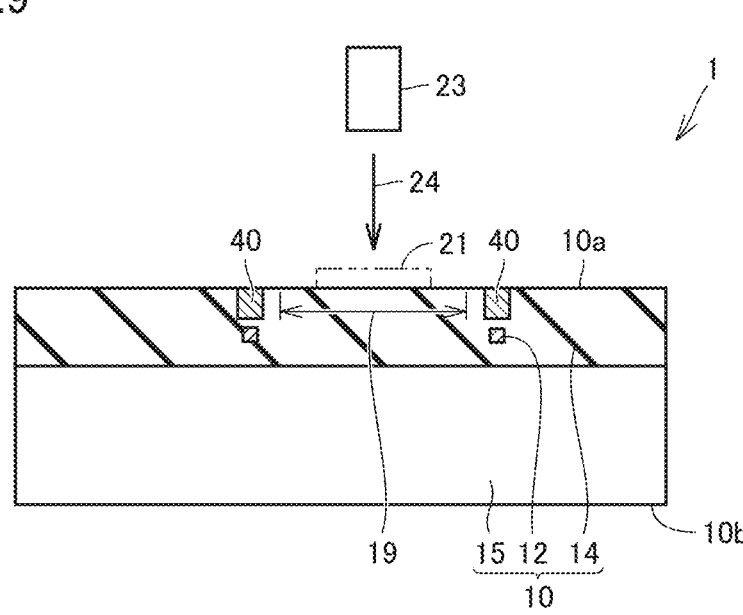
FIG. 9 is a schematic cross-sectional view of the non-invasive substance analyzer according to the third embodiment taken along a cross-sectional line IX-IX illustrated in FIG. 8.

With reference to FIGS. 8 and 9, the non-invasive substance analyzer 1c of the present embodiment includes a thermoregulator 40 that regulates a temperature of the waveguide-type ring resonator 12. The thermoregulator 40 is, for example, a heater such as a heater electrode. When a current is applied to the heater, the heater generates heat to change the temperature of the waveguide-type ring resonator 12. The heater is made of, for example, a high-resistance metal material such as tantalum, platinum, or titanium. The thermoregulator 40 is disposed closer to the main surface 10a than the waveguide-type ring resonator 12. The thermoregulator 40 is separated from the waveguide-type ring resonator 12 by the cladding layer 14.

The thermoregulator 40 has a band shape along the circumferential direction of the waveguide-type ring resonator 12 in a plan view of the main surface 10a. In the plan view of the main surface 10a, the length of the thermoregulator 40 in the circumferential direction of the waveguide-type ring resonator 12 is, for example, 50% or less of the length of the waveguide-type ring resonator 12 in the circumferential direction of the waveguide-type ring resonator 12. Therefore, the thermoregulator 40 is prevented from supplying excessive heat to the optical waveguide circuit 10 as compared with the absorption heat in the sample 21. Thus, it is possible to prevent the detection sensitivity of the absorption heat in the sample 21 from being significantly reduced by the thermoregulator 40. The length of the thermoregulator 40 in the circumferential direction of the waveguide-type ring resonator 12 may be 20% or less of the length of the waveguide-type ring resonator 12 in the circumferential direction of the waveguide-type ring resonator 12.

The phase of the waveguide-type ring resonator 12 is given by the equation (1) of the first embodiment. Therefore, as illustrated in FIG. 10, when the thermoregulator 40 is used to regulate the temperature of the waveguide-type ring resonator 12, the initial phase of the waveguide-type ring resonator 12 (the phase of the waveguide-type ring resonator 12 when the excitation light 24 is turned off) changes. In the present embodiment, the temperature of the thermoregulator 40 is set in such a manner that the change in the intensity of the first light 27a due to the ON/OFF of the excitation light 24 becomes greater. Thus, the initial phase of the waveguide-type ring resonator 12 is set.

Figure 10:
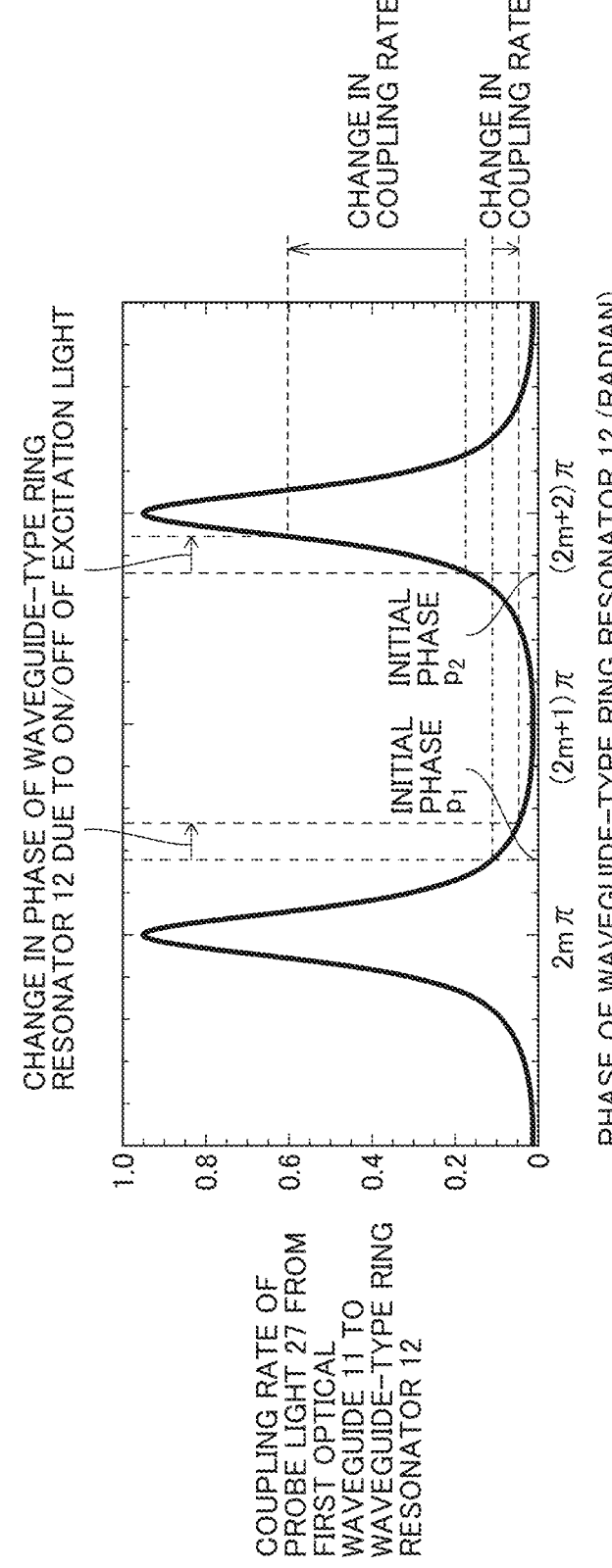
FIG. 10 is a graph illustrating a relationship between a phase of a waveguide-type ring resonator and a coupling rate of probe light from a first optical waveguide to the waveguide-type ring resonator.

For example, with reference to FIG. 10, when the thermoregulator 40 is turned off, the waveguide-type ring resonator 12 has an initial phase of p1. In the waveguide-type ring resonator 12 having an initial phase of p1, the change in the coupling rate of the probe light 27 from the first optical waveguide 11 to the waveguide-type ring resonator 12 due to the ON/OFF of the excitation light 24 is small, and thereby the change in the intensity of the first light 27a due to the ON/OFF of the excitation light 24 is small.

The thermoregulator 40 is used to regulate the temperature of the waveguide-type ring resonator 12 so as to set the initial phase of the waveguide-type ring resonator 12 to p2. In the waveguide-type ring resonator 12 having an initial phase of p2, the change in the coupling rate of the probe light 27 from the first optical waveguide 11 to the waveguide-type ring resonator 12 due to the ON/OFF of the excitation light 24 becomes greater, and thereby the change in the intensity of the first light 27a due to the ON/OFF of the excitation light 24 becomes greater. Therefore, the absorption heat in the sample 21 can be detected with higher accuracy. Accordingly, the substance in the sample 21 or on the surface of the sample 21 can be analyzed with higher accuracy.

A non-invasive substance analysis method of the present embodiment using the non-invasive substance analyzer 1c will be described with reference mainly to FIG. 11. The non-invasive substance analysis method of the present embodiment is similar to the non-invasive substance analysis method of the first embodiment (see FIG. 5), but is different from the non-invasive substance analysis method of the first embodiment in the following points.

The non-invasive substance analysis method according to the present embodiment further includes regulating the initial phase of the waveguide-type ring resonator 12 by using the thermoregulator 40 (S2) between step S1 and step S3. Specifically, the intensity of the first light 27a is measured using the light intensity detector 30 while changing the temperature of the waveguide-type ring resonator 12 using the thermoregulator 40 without irradiating the sample 21 with the excitation light 24. The temperature of the thermoregulator 40 is set in such a manner that a ratio of the change in the intensity of the first light 27a to the change in the temperature of the thermoregulator 40 (i.e., the change in the temperature of the waveguide-type ring resonator 12) becomes greater, preferably the ratio becomes maximum. Thus, the initial phase of the waveguide-type ring resonator 12 is set.

The non-invasive substance analyzer 1c of the present embodiment further exhibits the following effects in addition to the effects of the non-invasive substance analyzer 1 of the first embodiment.

The non-invasive substance analyzer 1c according to the present embodiment further includes a thermoregulator 40 that regulates a temperature of the waveguide-type ring resonator 12.

By regulating the temperature of the waveguide-type ring resonator 12 using the thermoregulator 40, the initial phase of the waveguide-type ring resonator 12 (the phase of the waveguide-type ring resonator 12 when the excitation light 24 is turned off) can be set in such a manner that the change in the intensity of the first light 27a due to the ON/OFF of the excitation light 24 becomes greater. Therefore, the substance in the sample 21 or on the surface of the sample 21 can be analyzed with higher accuracy.

In the non-invasive substance analyzer 1c of the present embodiment, in a plan view of the first main surface (the main surface 10a), the length of the thermoregulator 40 in the circumferential direction of the waveguide-type ring resonator 12 is 50% or less of the length of the waveguide-type ring resonator 12 in the circumferential direction of the waveguide-type ring resonator 12.

Therefore, the thermoregulator 40 is prevented from supplying excessive heat to the optical waveguide circuit 10 as compared with the absorption heat in the sample 21. Thus, it is possible to prevent the detection sensitivity of the absorption heat in the sample 21 from being significantly reduced by the thermoregulator 40. Therefore, the substance in the sample 21 or on the surface of the sample 21 can be analyzed with higher accuracy.

Fourth Embodiment

A non-invasive substance analyzer 1d according to a fourth embodiment will be described with reference to FIG. 12. The non-invasive substance analyzer 1d of the present embodiment has a configuration similar to that of the non-invasive substance analyzer 1 of the first embodiment, but is mainly different in the following points.

The non-invasive substance analyzer 1d further includes a thermoregulator 42 that regulates a temperature of the probe light source 26. The thermoregulator 42 is, for example, a heater or a Peltier element. When the temperature of the probe light source 26 is changed by the thermoregulator 42, the wavelength of the probe light 27 emitted from the probe light source 26 changes.

Since the phase of the waveguide-type ring resonator 12 is given by the equation (1) of the first embodiment, when the wavelength of the probe light 27 changes, the initial phase of the waveguide-type ring resonator 12 (the phase of the waveguide-type ring resonator 12 when the excitation light 24 is turned off) changes. In the present embodiment, the thermoregulator 42 is used to regulate the temperature of the probe light source 26 so as to regulate the wavelength of the probe light 27. The wavelength of the probe light 27 is set in such a manner that the change in the intensity of the first light 27a due to the ON/OFF of the excitation light 24 becomes greater. Thus, the initial phase of the waveguide-type ring resonator 12 is set.

The non-invasive substance analyzer 1d of the present embodiment further exhibits the following effects in addition to the effects of the non-invasive substance analyzer 1 of the first embodiment.

The non-invasive substance analyzer 1*d* of the present embodiment further includes a thermoregulator 42 that regulates a temperature of the probe light source 26.

The thermoregulator 42 is used to regulate the temperature of the probe light source 26 so as to regulate the wavelength of the probe light 27. By regulating the wavelength of the probe light 27, the initial phase of the waveguide-type ring resonator 12 (the phase of the waveguide-type ring resonator 12 when the excitation light 24 is turned off) can be set in such a manner that the change in the intensity of the first light 27*a* due to the ON/OFF of the excitation light 24 becomes greater. Thus, the substance in the sample 21 or on the surface of the sample 21 can be analyzed with higher accuracy.

Fifth Embodiment

Figures 13, 14:
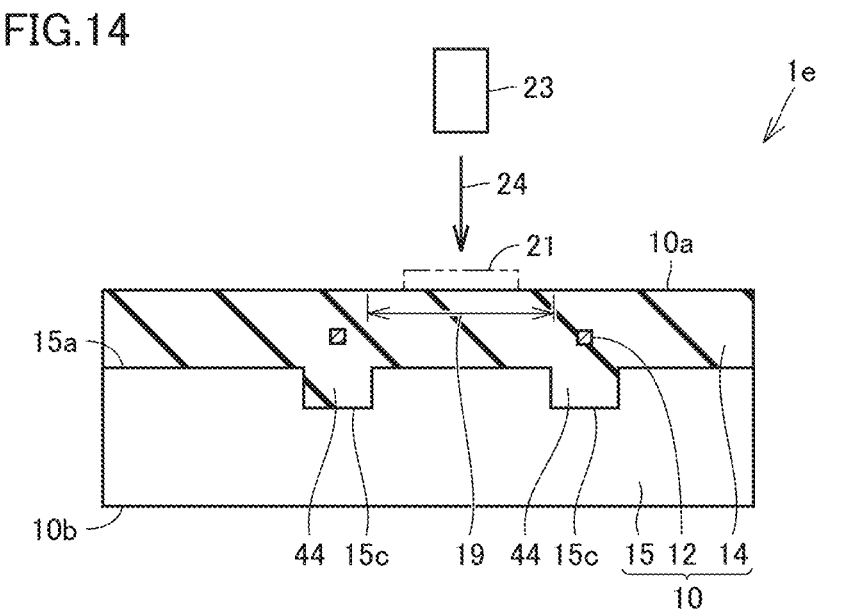
FIG. 13 is a schematic plan view of a non-invasive substance analyzer according to a fifth embodiment.
FIG. 14 is a schematic cross-sectional view of the non-invasive substance analyzer according to the fifth embodiment taken along a cross-sectional line XIV-XIV illustrated in FIG. 13.

A non-invasive substance analyzer 1*e* according to a fifth embodiment will be described with reference to FIGS. 13 and 14. The non-invasive substance analyzer 1*e* of the present embodiment has a configuration similar to that of the non-invasive substance analyzer 1 of the first embodiment, but is mainly different in the following points.

In the present embodiment, the optical waveguide circuit 10 is provided with a recess 15*c* on a surface 15*a* of the substrate 15 facing the waveguide-type ring resonator 12. The recess 15*c* faces the waveguide-type ring resonator 12 in the thickness direction of the optical waveguide circuit 10 (the direction in which the main surface 10*a* and the main surface 10*b* face each other). The recess 15*c* is formed by cutting or etching the substrate 15. In a plan view of the main surface 10*a*, the recess 15*c* overlaps with the waveguide-type ring resonator 12.

The optical waveguide circuit 10 includes a thermal insulation member 44, The recess 15*c* is filled with the thermal insulation member 44. The thermal insulation member 44 has a smaller thermal conductivity than the substrate 15. In the present embodiment, the thermal insulation member 44 is made of the same material (for example, silica glass) as that of the cladding layer 14. The thermal insulation member 44 may be made of a material having a smaller thermal conductivity than the substrate 15, and may be made of a material different from that of the cladding layer 14. The thermal insulation member 44 faces the waveguide-type ring resonator 12 in the thickness direction of the optical waveguide circuit 10 (the direction in which the main surface 10*a* and the main surface 10*b* face each other).

The non-invasive substance analyzer 1*e* of the present embodiment further exhibits the following effects in addition to the effects of the non-invasive substance analyzer 1 of the first embodiment.

In the non-invasive substance analyzer 1*e* of the present embodiment, the optical waveguide circuit 10 includes a substrate 15 which supports the waveguide-type ring resonator 12 and a thermal insulation member 44 which has a smaller thermal conductivity than the substrate 15. A recess 15*c* that overlaps with the waveguide-type ring resonator 12 in a plan view of the first main surface (main surface 10*a*) is provided on a surface 15*a* of the substrate 15 facing the waveguide-type ring resonator 12. The recess 15*c* is filled with the thermal insulation member 44.

The thermal insulation member 44 makes it difficult for the absorption heat in the sample 21 to escape to the substrate 15. The change in the intensity of the first light 27*a* due to the ON/OFF of the excitation light 24 becomes greater. Therefore, the non-invasive substance analyzer 1*e* can analyze the substance in the sample 21 or on the surface of the sample 21 with higher accuracy.

Sixth Embodiment

Figure 15:
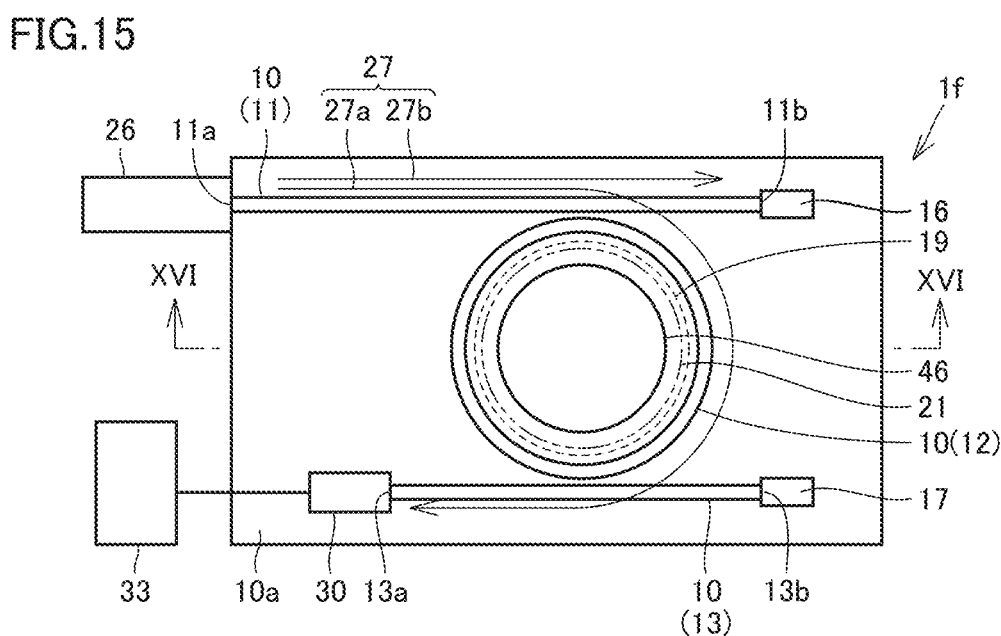
FIG. 15 is a schematic plan view of a non-invasive substance analyzer according to a sixth embodiment.
Figure 16:
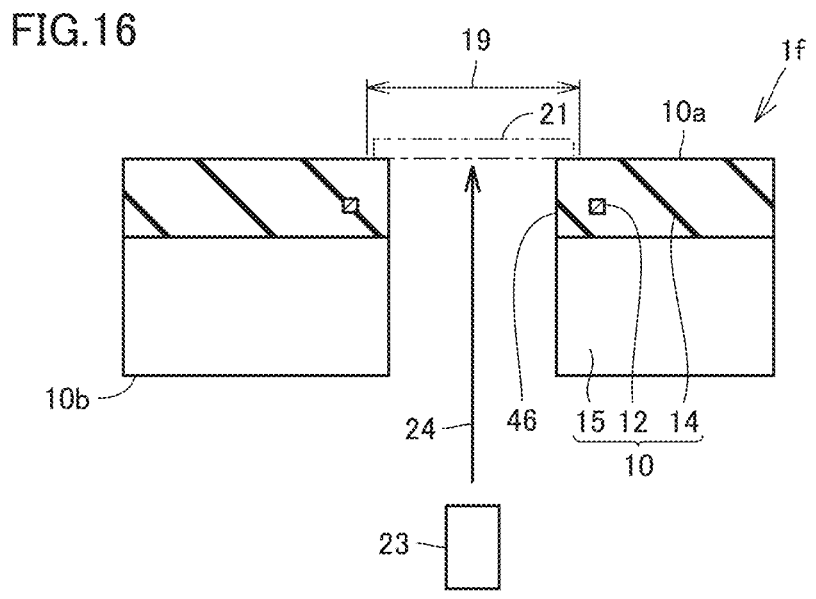
FIG. 16 is a schematic cross-sectional view of the non-invasive substance analyzer according to the sixth embodiment taken along a cross-sectional line XVI-XVI illustrated in FIG. 15.

A non-invasive substance analyzer 1*f* according to a sixth embodiment will be described with reference to FIGS. 15 and 16. The non-invasive substance analyzer 1*f* of the present embodiment has a configuration similar to that of the non-invasive substance analyzer 1 of the first embodiment, but is mainly different in the following points.

In the non-invasive substance analyzer 1*f*, a through hole 46 is provided in the optical waveguide circuit 10. The through hole 46 extends from the sample mounting region 19 to the main surface 10*b* and penetrates the optical waveguide circuit 10. The through hole 46 is located inside the waveguide-type ring resonator 12. The excitation light 24 passes through the through hole 46, and is irradiated on the sample 21. In the present embodiment, in a plan view of the main surface 10*a*, the size of the sample 21 is larger than the size of the through hole 46.

The non-invasive substance analyzer 1*f* of the present embodiment further exhibits the following effects in addition to the effects of the non-invasive substance analyzer 1 of the first embodiment.

In the non-invasive substance analyzer 1*f* of the present embodiment, a through hole 46 that extends from the sample mounting region 19 to the second main surface (the main surface 10*b*) is provided in the optical waveguide circuit 10. The excitation light 24 passes through the through hole 46, and is irradiated on the sample 21.

The through hole 46 through which the excitation light 24 passes is provided in the optical waveguide circuit 10. Therefore, the excitation light 24 is not absorbed by the optical waveguide circuit 10, and thereby reaches the sample 21 with stronger light intensity. The absorption heat in the sample 21 increases. In addition, it is difficult for the absorption heat in the sample 21 to escape in the thickness direction of the optical waveguide circuit 10 (the direction in which the main surface 10*a* and the main surface 10*b* face each other). The change in the intensity of the first light 27*a* due to the ON/OFF of the excitation light 24 becomes greater. Therefore, the substance in the sample 21 or on the surface of the sample 21 can be analyzed with higher accuracy.

Even if the optical waveguide circuit 10 (the substrate 15) is made of a material opaque to the excitation light 24, the excitation light 24 can be irradiated toward the sample 21 from the side of the main surface 10*b*. This expands the choice of materials for the optical waveguide circuit 10 (the substrate 15) and increases the degree of freedom of arranging the excitation light source 23.

Seventh Embodiment

Figures 17, 18:
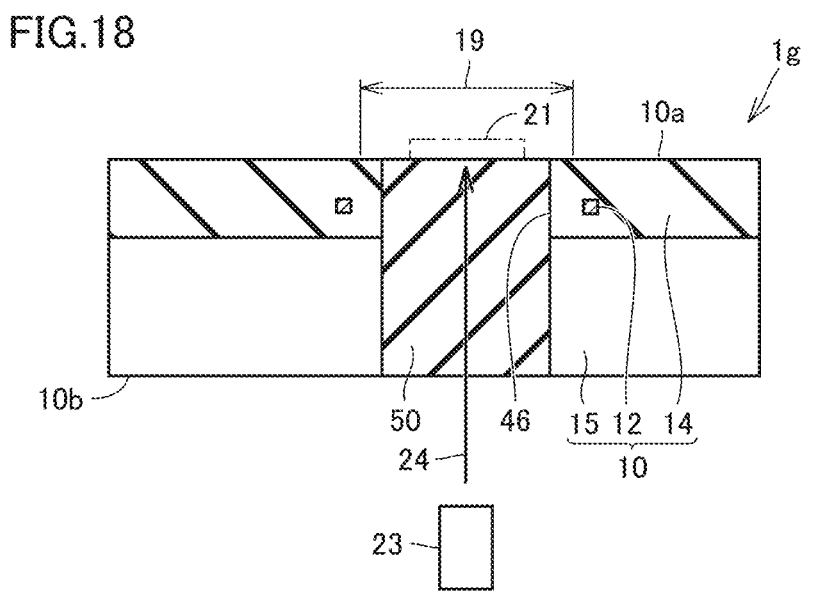
FIG. 17 is a schematic plan view of a non-invasive substance analyzer according to a seventh embodiment.
FIG. 18 is a schematic cross-sectional view of the non-invasive substance analyzer according to the seventh embodiment taken along a cross-sectional line XVIII-XVIII illustrated in FIG. 17.

A non-invasive substance analyzer 1*g* according to a seventh embodiment will be described with reference to FIGS. 17 and 18. The non-invasive substance analyzer 1*g* of the present embodiment has a configuration similar to that of the non-invasive substance analyzer 1*f* of the sixth embodiment, but is mainly different in the following points.

The non-invasive substance analyzer 1*g* further includes an optical medium 50. The optical medium 50 transmits the excitation light 24. The transmittance of the optical medium 50 with respect to the excitation light 24 is greater than the transmittance of the optical waveguide circuit 10 (the substrate 15) with respect to the excitation light 24. The excitation light 24 passes through the optical medium 50, and is irradiated on the sample 21. When the excitation light 24 is mid-infrared light, the optical medium 50 is made of a material transparent to the mid-infrared light, such as germanium (Ge), zinc selenide (ZnSe), zinc sulfide (ZnS), or chalcogenide glass (SSbSnGe).

The optical medium 50 closes the through hole 46. At least a part of the sample mounting region 19 is formed by the optical medium 50. The sample 21 may be mounted on the optical medium 50. The through hole 46 is filled with the optical medium 50. The optical medium 50 extends from the sample mounting region 19 to the main surface 10b. The thermal conductivity of the optical medium 50 is greater than the thermal conductivity of air. Therefore, the absorption heat in the sample 21 is efficiently conducted to the waveguide-type ring resonator 12 through the optical medium 50. The thermal conductivity of the optical medium 50 may be greater than the thermal conductivity of the cladding layer 14. The thermal conductivity of the optical medium 50 is smaller than the thermal conductivity of the substrate 15. Therefore, it is difficult for the absorption heat in the sample 21 to escape in the thickness direction of the optical waveguide circuit 10 (the direction in which the main surface 10a and the main surface 10b face each other).

Figure 19:
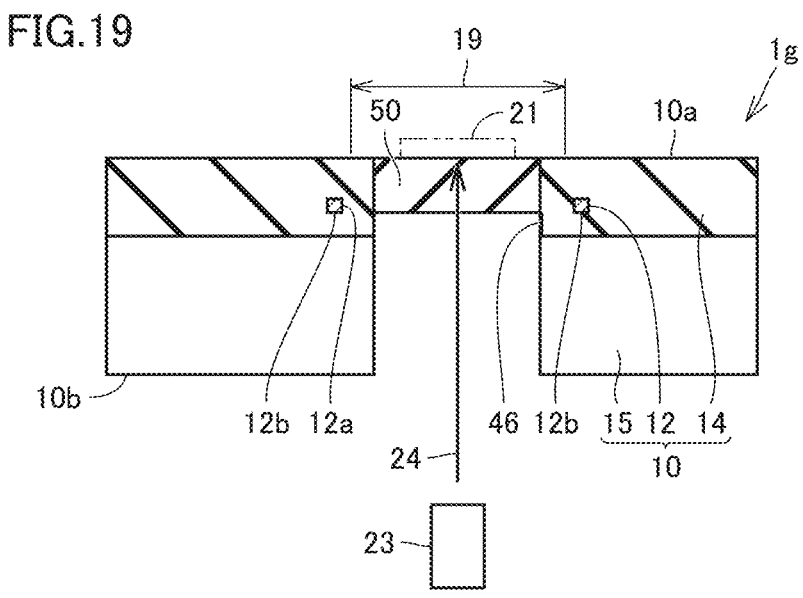
FIG. 19 is a schematic cross-sectional view of a non-invasive substance analyzer according to a modification of the seventh embodiment.

With reference to FIG. 19, in a modification of the present embodiment, the optical medium 50 extends from sample mounting region 19 to a height of an inner side surface 12a of the waveguide-type ring resonator 12 in the thickness direction of the optical waveguide circuit 10 (the direction in which the main surface 10a and the main surface 10b face each other). In other words, the optical medium 50 faces at least a part of the inner side surface 12a of the waveguide-type ring resonator 12. The optical medium 50 may extend from the sample mounting region 19 to a height of a lower surface 12b of the waveguide-type ring resonator 12 in the thickness direction of the optical waveguide circuit 10. In other words, the optical medium 50 may face the entire inner side surface 12a of the waveguide-type ring resonator 12. The lower surface 12b of the waveguide-type ring resonator 12 faces the main surface 10b.

A portion of the through hole 46 that is closer to the main surface 10b than the optical medium 50 is a cavity that is not filled with the optical medium 50. The excitation light 24 passes through the cavity and the optical medium 50, and is irradiated on the sample 21. The optical medium 50 is separated from the substrate 15, which makes it difficult for the absorption heat in the sample 21 to escape to the substrate 15 through the optical medium 50. Therefore, the optical medium 50 may be made of a material having a greater thermal conductivity than the cladding layer 14. For example, the optical medium 50 may be made of a material having a thermal conductivity of 10 W/(m·K) or more, such as germanium (Ge), zinc selenide (ZnSe), or zinc sulfide (ZnS). Therefore, the absorption heat in the sample 21 is efficiently conducted to the waveguide-type ring resonator 12 through the optical medium 50.

The non-invasive substance analyzer 1g of the present embodiment further exhibits the following effects similar to the effects of the non-invasive substance analyzer 1f of the sixth embodiment.

The non-invasive substance analyzer 1g of the present embodiment further includes an optical medium 50 that transmits the excitation light 24. The optical medium 50 closes the through hole 46. The excitation light 24 passes through the optical medium 50, and is irradiated on the sample 21.

Since the excitation light 24 passes through the optical medium 50, it reaches the sample 21 with stronger light intensity. The absorption heat in the sample 21 is efficiently conducted to the waveguide-type ring resonator 12 through the optical medium 50. The change in the intensity of the first light 27a due to the ON/OFF of the excitation light 24 becomes greater. Therefore, the substance in the sample 21 or on the surface of the sample 21 can be analyzed with higher accuracy.

The sample 21 may be mounted on the optical medium 50. Thus, the substance in the sample 21 or on the surface of the sample 21 can be analyzed even if the size of the sample 21 is smaller than the size of the through hole 46 or even if the sample 21 is liquid.

In the non-invasive substance analyzer 1g of the present embodiment, the optical medium 50 extends from the sample mounting region 19 to the height of the inner side surface 12a of the waveguide-type ring resonator 12. A portion of the through hole 46 that is closer to the second main surface (the main surface 10b) than the optical medium 50 is a cavity that is not filled with the optical medium 50.

Since the excitation light 24 is not attenuated in the cavity, the excitation light 24 reaches the sample 21 with stronger light intensity. The absorption heat in the sample 21 increases. In addition, since the thermal conductivity of air in the cavity is low, the cavity makes it difficult for the absorption heat in the sample 21 to escape from the waveguide-type ring resonator 12. Therefore, the change in the intensity of the first light 27a due to ON/OFF of the excitation light 24 becomes greater. Therefore, the substance in the sample 21 or on the surface of the sample 21 can be analyzed with higher accuracy.

Eighth Embodiment

Figure 20:
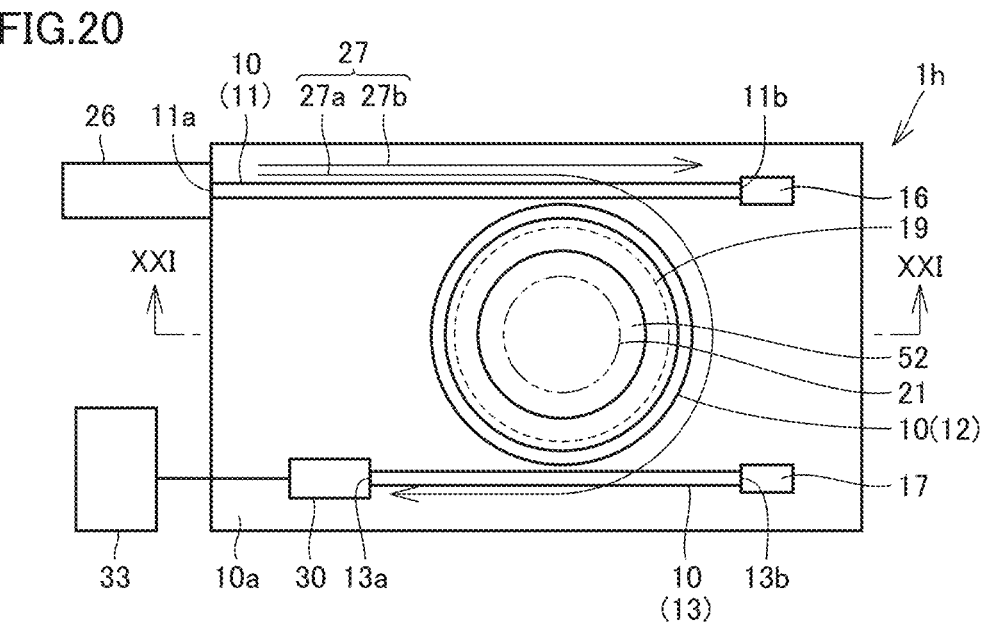
FIG. 20 is a schematic plan view of a non-invasive substance analyzer according to an eighth embodiment.
Figure 21:
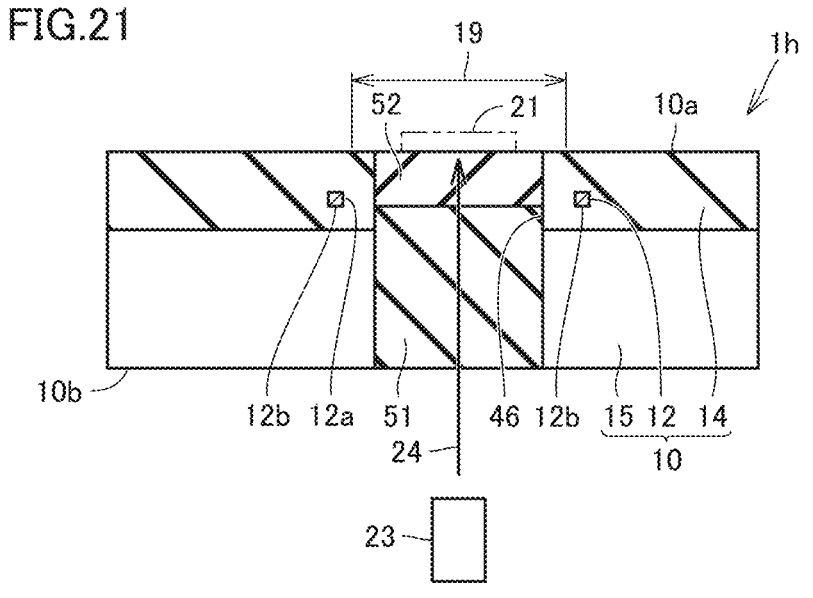
FIG. 21 is a schematic cross-sectional view of the non-invasive substance analyzer of the eighth embodiment taken along a cross-sectional line XXI-XXI illustrated in FIG. 20.

A non-invasive substance analyzer 1h according to an eighth embodiment will be described with reference to FIGS. 20 and 21. The non-invasive substance analyzer 1h of the present embodiment has a configuration similar to that of the non-invasive substance analyzer 1g of the seventh embodiment, but is mainly different in the following points.

The non-invasive substance analyzer 1h of the present embodiment includes a first optical medium 51 and a second optical medium 52 instead of the optical medium 50. The first optical medium 51 and the second optical medium 52 transmit the excitation light 24. The transmittance of the first optical medium 51 with respect to the excitation light 24 is greater than the transmittance of the optical waveguide circuit 10 (specifically the substrate 15) with respect to the excitation light 24. The transmittance of the second optical medium 52 with respect to the excitation light 24 is greater than the transmittance of the optical waveguide circuit 10 (specifically the substrate 15) with respect to the excitation light 24. The first optical medium 51 closes the through hole 46. The second optical medium 52 closes the through hole 46. The second optical medium 52 is disposed closer to the sample mounting region 19 than the first optical medium 51. At least a part of the sample mounting region 19 is formed by the second optical medium 52. The sample 21 may be mounted on the second optical medium 52. The excitation light 24 passes through the first optical medium 51 and the second optical medium 52, and is irradiated on the sample 21.

The first optical medium 51 has a lower thermal conductivity than the second optical medium 52. The first optical medium 51 separates the second optical medium 52 from the substrate 15. Therefore, it is difficult for the absorption heat in the sample 21 to escape in the thickness direction of the optical waveguide circuit 10. The first optical medium 51 may have, for example, a thermal conductivity of 5 W/(m·K) or less, or may have a thermal conductivity of 1 W/(m·K) or less. When the excitation light 24 is mid-infrared light, the first optical medium 51 is made of, for example, chalcogenide glass (SSbSnGe).

The second optical medium 52 has a higher thermal conductivity than the first optical medium 51. Therefore, the absorption heat in the sample 21 is efficiently conducted to the waveguide-type ring resonator 12 through the second optical medium 52. Since the second optical medium 52 is separated from the substrate 15, it is difficult for the absorption heat in the sample 21 to escape to the substrate 15. Therefore, the second optical medium 52 may be made of a material having a greater thermal conductivity than the cladding layer 14. For example, the second optical medium 52 may have a thermal conductivity of 10 W/(m·K) or more, or may have a thermal conductivity of 15 W/(m·K) or more. When the excitation light 24 is mid-infrared light, the second optical medium 52 is made of, for example, germanium (Ge), zinc selenide (ZnSe), or zinc sulfide (ZnS).

The second optical medium 52 extends from the sample mounting region 19 to the height of the inner side surface 12a of the waveguide-type ring resonator 12 in the thickness direction of the optical waveguide circuit 10 (the direction in which the main surface 10a and the main surface 10b face each other). In other words, the second optical medium 52 faces at least a part of the inner side surface 12a of the waveguide-type ring resonator 12. The second optical medium 52 may extend from the sample mounting region 19 to the height of the lower surface 12b of the waveguide-type ring resonator 12 in the thickness direction of the optical waveguide circuit 10. In other words, the second optical medium 52 may face the entire inner side surface 12a of the waveguide-type ring resonator 12.

The non-invasive substance analyzer 1h of the present embodiment further exhibits the following effects similar to the effects of the non-invasive substance analyzer 1g of the seventh embodiment.

The non-invasive substance analyzer 1h of the present embodiment further includes a first optical medium 51 that transmits the excitation light 24 and a second optical medium 52 that transmits the excitation light 24. The first optical medium 51 closes the through hole 46. The second optical medium 52 closes the through hole 46, has a higher thermal conductivity than the first optical medium 51, and is disposed closer to the sample mounting region 19 than the first optical medium 51. The excitation light 24 passes through the first optical medium 51 and the second optical medium 52, and is irradiated on the sample 21.

The absorption heat in the sample 21 is efficiently conducted to the waveguide-type ring resonator 12 through the second optical medium 52. However, the first optical medium 51 makes it difficult for the absorption heat in the sample 21 to escape from the waveguide-type ring resonator 12. The change in the intensity of the first light 27a due to the ON/OFF of the excitation light 24 becomes greater. Therefore, the substance in the sample 21 or on the surface of the sample 21 can be analyzed with higher accuracy.

The sample 21 may be mounted on the second optical medium 52. Thus, the substance in the sample 21 or on the surface of the sample 21 can be analyzed even if the size of the sample 21 is smaller than the size of the through hole 46 or even if the sample 21 is liquid.

In the non-invasive substance analyzer 1h of the present embodiment, the second optical medium 52 extends from the sample mounting region 19 to the height of the inner side surface 12a of the waveguide-type ring resonator 12.

The absorption heat in the sample 21 is more efficiently conducted to the waveguide-type ring resonator 12 through the optical medium 50. Therefore, the change in the intensity of the first light 27a due to ON/OFF of the excitation light 24 becomes greater. Therefore, the substance in the sample 21 or on the surface of the sample 21 can be analyzed with higher accuracy.

In the non-invasive substance analyzer 1h of the present embodiment, the second optical medium 52 extends from the sample mounting region 19 to the height of the lower surface 12b of the waveguide-type ring resonator 12. The lower surface 12b of the waveguide-type ring resonator 12 faces the second main surface (the main surface 10b).

The absorption heat in the sample 21 is more efficiently conducted to the waveguide-type ring resonator 12 through the optical medium 50. Therefore, the change in the intensity of the first light 27a due to ON/OFF of the excitation light 24 becomes greater. Therefore, the substance in the sample 21 or on the surface of the sample 21 can be analyzed with higher accuracy.

It should be understood that the first to eighth embodiments disclosed herein are illustrative and non-restrictive in all respects. At least two of the first to eighth embodiments disclosed herein may be combined as long as there is no contradiction. The scope of the present disclosure is defined the claims rather than the above description, and is intended to include all modifications within the meaning and scope equivalent to the claims.

REFERENCE SIGNS LIST

1, 1b, 1c, 1d, 1e, 1f, 1g, 1h: non-invasive substance analyzer; 10: optical waveguide circuit; 10a, 10b: main surface; 11: first optical waveguide; 11a, 11b, 13a, 13b: end; 12: waveguide-type ring resonator; 12a: inner side surface; 12b: lower surface; 13: second optical waveguide; 14: cladding layer; 15: substrate; 15a: surface; 15c: recess; 16, 17: termination portion; 19: sample mounting region; 21; sample; 23: excitation light source; 24: excitation light; 26: probe light source; 27: probe light; 27a: first light; 27b: second light; 30, 31: light intensity detector; 33: substance analyzer; 40, 42: thermoregulator; 44: thermal insulation member; 46: through hole; 50: optical medium; 51: first optical medium; 52: second optical medium.

The invention claimed is:

1. A non-embedded type non-invasive substance analyzer for analyzing substance included in a human body without being embedded in the human body to check a blood glucose level, the non-invasive substance analyzer comprising:

an optical waveguide circuit having a first main surface including a sample mounting region and a second main surface opposite to the first main surface;

an excitation light source that emits excitation light toward a sample mounted on the sample mounting region from a vertical direction with respect to the sample mounting region;

a probe light source that emits probe light;

a first light intensity detector; and a second light intensity detector, wherein the optical waveguide circuit includes a first optical waveguide to which the probe light is incident from one end side to the other end side, a waveguide-type ring resonator which is optically coupled to the first optical waveguide, and a second optical waveguide which is optically coupled to the waveguide-type ring resonator and in which the probe light via the waveguide-type ring resonator propagates from the other end side to the one end side, in a plan view of the first main surface, the sample mounting region to which the excitation light is emitted from the excitation light source in the vertical direction is located inside the waveguide-type ring resonator, the probe light source and the first light intensity detector are located on the one end side with respect to the sample mounting region and the waveguide-type ring resonator, the first light intensity detector is optically coupled to the second optical waveguide on the one end side and detects an intensity of first light which is a part of the probe light and is optically coupled to the second optical waveguide, and the second light intensity detector is optically coupled to the first optical waveguide, and detects an intensity of second light which is a part of the probe light and propagates in the first optical waveguide without being coupled to the waveguide-type ring resonator.

2. The non-invasive substance analyzer according to claim 1 further comprising:

a substance analysis unit that analyzes a substance in the sample or on a surface of the sample based on a difference between the intensity of the first light and the intensity of the second light.

3. The non-invasive substance analyzer according to claim 1 further comprising:

a second thermoregulator that regulates a temperature of the probe light source.

4. The non-invasive substance analyzer according to claim 1, wherein a through hole that extends from the sample mounting region to the second main surface is provided in the optical waveguide circuit, and the excitation light passes through the through hole, and is irradiated on the sample.

5. The non-invasive substance analyzer according to claim 4 further comprising:

an optical medium that transmits the excitation light, wherein the optical medium closes the through hole, and the excitation light passes through the optical medium, and is irradiated on the sample.

6. The non-invasive substance analyzer according to claim 5, wherein the optical medium extends from the sample mounting region to a height of an inner side surface of the waveguide-type ring resonator, and a portion of the through hole that is closer to the second main surface than the optical medium is a cavity that is not filled with the optical medium.

7. The non-invasive substance analyzer according to claim 4 further comprising:

a first optical medium that transmits the excitation light; and a second optical medium that transmits the excitation light, wherein the first optical medium closes the through hole, the second optical medium closes the through hole, has a higher thermal conductivity than the first optical medium, and is disposed closer to the sample mounting region than the first optical medium, and the excitation light passes through the first optical medium and the second optical medium, and is irradiated on the sample.

8. The non-invasive substance analyzer according to claim 7, wherein the second optical medium extends from the sample mounting region to a height of an inner side surface of the waveguide-type ring resonator.

9. The non-invasive substance analyzer according to claim 7, wherein the second optical medium extends from the sample mounting region to a height of a lower surface of the waveguide-type ring resonator, and the lower surface of the waveguide-type ring resonator faces the second main surface.

10. The non-invasive substance analyzer according to claim 1, wherein the optical waveguide circuit includes a first termination portion, the second optical waveguide includes a first end optically coupled to the first light intensity detector and a second end opposite to the first end, and the first termination portion is provided at the second end of the second optical waveguide, and scatters or absorbs the probe light.

11. The non-invasive substance analyzer according to claim 1, wherein the waveguide-type ring resonator is a silicon waveguide.

12. A non-embedded type non-invasive substance analyzer for analyzing substance included in a human body without being embedded in the human body to check a blood glucose level, the non-invasive substance analyzer comprising:

an optical waveguide circuit having a first main surface including a sample mounting region and a second main surface opposite to the first main surface;

an excitation light source that emits excitation light toward a sample mounted on the sample mounting region from a vertical direction with respect to the sample mounting region;

a probe light source that emits probe light;

a first light intensity detector; and a first thermoregulator, wherein the optical waveguide circuit includes a first optical waveguide to which the probe light is incident from one end side to the other end side, a waveguide-type ring resonator which is optically coupled to the first optical waveguide, and a second optical waveguide which is optically coupled to the waveguide-type ring resonator and in which the probe light via the waveguide-type ring resonator propagates from the other end side to the one end side, in a plan view of the first main surface, the sample mounting region to which the excitation light is emitted from the excitation light source in the vertical direction is located inside the waveguide-type ring resonator, the probe light source and the first light intensity detector are located on the one end side with respect to the sample mounting region and the waveguide-type ring resonator, the first light intensity detector is optically coupled to the second optical waveguide on the one end side and detects an intensity of first light which is a part of the probe light and is optically coupled to the second optical waveguide, and the first thermoregulator regulates a temperature of the waveguide-type ring resonator.

13. The non-invasive substance analyzer according to claim 12, wherein

23 in a plan view of the first main surface, a length of the first thermoregulator in a circumferential direction of the waveguide-type ring resonator is 50% or less of a length of the waveguide-type ring resonator in the circumferential direction.

14. The non-invasive substance analyzer according to claim 12 further comprising:

a substance analysis unit that analyzes a substance in the sample or on a surface of the sample based on the intensity of the first light.

15. The non-invasive substance analyzer according to claim 12, wherein the optical waveguide circuit includes a first termination portion and a second termination portion, the second optical waveguide includes a first end optically coupled to the first light intensity detector and a second end opposite the first end, the first termination portion is provided at the second end of the second optical waveguide, and scatters or absorbs the probe light, the first optical waveguide includes a third end to which the probe light is incident and a fourth end opposite to the third end, and the second termination portion is provided at the fourth end of the first optical waveguide, and scatters or absorbs the probe light.

16. A non-embedded type non-invasive substance analyzer for analyzing substance included in a human body without being embedded in the human body to check a blood glucose level, the non-invasive substance analyzer comprising:

an optical waveguide circuit having a first main surface including a sample mounting region and a second main surface opposite to the first main surface;

an excitation light source that emits excitation light toward a sample mounted on the sample mounting region from a vertical direction with respect to the sample mounting region;

a probe light source that emits probe light; and a first light intensity detector, wherein the optical waveguide circuit includes a first optical waveguide to which the probe light is incident from one end side to the other end side, a waveguide-type ring resonator which is optically coupled to the first optical waveguide, a second optical waveguide which is optically coupled to the waveguide-type ring resonator and in which the probe light via the waveguide-type ring resonator propagates from the other end side to the one end side, a substrate which supports the waveguide-type ring resonator, and a thermal insulation member which has a smaller thermal conductivity than the substrate, in a plan view of the first main surface, the sample mounting region to which the excitation light is emitted from the excitation light source in the vertical direction is located inside the waveguide-type ring resonator, a recess that overlaps with the waveguide-type ring resonator in a plan view of the first main surface is provided on a surface of the substrate facing the waveguide-type ring resonator, the recess is filled with the thermal insulation member, the probe light source and the first light intensity detector are located on the one end side with respect to the sample mounting region and the waveguide-type ring resonator, and the first light intensity detector is optically coupled to the second optical waveguide on the one end side and detects an intensity of first light which is a part of the probe light and is optically coupled to the second optical waveguide.

* * * * *